United States Patent [19]

Newman et al.

[11] Patent Number: 5,516,634

[45] Date of Patent: May 14, 1996

[54] MOLECULAR BASIS OF THE HUMAN PLATELET BRA/BRB ALLOANTIGEN SYSTEM AND APPLICATIONS THEREOF

[76] Inventors: Peter J. Newman, 9485 N. Waverly Dr., Bayside, Wis. 53217; Sentot S. Santoso, Fliederstr. 10, Buseck, Germany, 35418

[21] Appl. No.: 86,634

[22] Filed: Jun. 30, 1993

[51] Int. Cl.[6] .............................. C12Q 1/68; C12P 19/34; C07H 21/04

[52] U.S. Cl. ..................... 435/6; 435/91.2; 435/91.5; 435/199; 536/23.5; 536/24.31; 536/24.33; 935/8; 935/17; 935/77; 935/78

[58] Field of Search ..................... 435/6, 91.2, 91.5, 435/199; 536/24.3, 24.33, 23.5; 436/63; 935/77, 78, 5, 81, 17; 514/44

[56] References Cited

PUBLICATIONS

Bochringer Mannhein Catalog, p.144, 1990/1991.
Santoso et al, Tissue Antigens (1989) 33(2):358.
Takada et al, J. Cell Biology (1989) 109:397–407.

*Primary Examiner*—W. Gary Jones
*Assistant Examiner*—Carla Myers
*Attorney, Agent, or Firm*—Foley & Lardner

[57] ABSTRACT

Based on the discovery of the amino acid and nucleotide differences which distinguish the $Br^a$ and $Br^b$ allelic forms of the membrane glycoprotein GPIa, and which comprise the diallelic Br platelet alloantigen system, compositions and methods are provided for determining the Br genotype and phenotype of individuals. Also provided, on the basis of this discovery, are compositions and methods for treating disorders associated with Br alloantigen incompatibility, such as the bleeding disorders post-transfusion purpura, post-transfusion platelet refractoriness, and neonatal alloimmune thrombocytopenic purpura. The two allelic forms of GPIa differ by a single amino acid. The $Br^a$ allelic form has Lys at position 505 in the sequence of the mature GPIa. The $Br^b$ allelic form has Glu at the same position. This amino acid difference is due to a single change, from A for the $Br^a$ allele to G for the $Br^b$ allele, in the GPIa gene.

16 Claims, No Drawings

MOLECULAR BASIS OF THE HUMAN PLATELET BRA/BRB ALLOANTIGEN SYSTEM AND APPLICATIONS THEREOF

TECHNICAL FIELD

The present invention provides novel compositions and methods for use in avoiding the occurrence of certain serious disorders, especially certain bleeding disorders, and novel compositions and methods for use in treating such a disorder, in a person in which the disorder has occurred, or avoiding such a disorder, in an individual who is susceptible thereto.

The novel compositions and methods of the invention are based on the discovery, which underlies the invention, of the basis, at the level of gene and protein sequences, for the disorders, which the invention concerns.

BACKGROUND OF THE INVENTION

Among the disorders, which the invention concerns, are those involving abnormal and excessive bleeding due to destruction of blood platelets ("platelets").

The disorders include post-transfusion purpura ("PTP") and post-transfusion platelet refractoriness ("PTPR"), which are suffered by some persons who receive blood or platelets from other persons by transfusion or the like.

The disorders also include one that is suffered by fetuses and newborns and is known as "neonatal alloimmune thrombocytopenic purpura" ("NATP"). This disorder can cause death of fetuses and serious birth defects or death of newborns. NATP is estimated to affect about 1 in 2000 newborns. In NATP, fetal platelets, which enter the mother's blood stream, induce production in the mother of antibodies against fetal platelets. These maternal antibodies then pass with the mother's blood into the fetus and mediate destruction of platelets in the fetus.

A mother, whose fetus or newborn suffers from NATP, is at increased risk of suffering PTP or PTPR.

When platelets from a first human (a "donor") are introduced into the blood system of a second human (a "recipient"), by transfusion, through the placenta (in the case of fetal blood entering the mother), or the like, the recipient may mount an immune response against the platelets from the donor. Such an immune response is referred to as an "alloimmune" response, because it involves antibodies reacting against antigens of the same species. The alloimmune response to platelets is due to an immune response of the recipient against "alloantigens" (antigens of the same species as that mounting the immune response) on platelets from the donor. These alloantigens are on membrane glycoproteins that occur in the membranes, which define the outer surfaces of platelets ("platelet membranes"). Each of these membrane glycoproteins typically has a cytoplasmic domain or segment, which is the part of the glycoprotein exposed to the cytoplasm inside the platelet; a transmembrane domain, which is the part of the glycoprotein embedded in the platelet membrane; and an extracellular domain or segment, which is the part of the glycoprotein exposed to the outside of the platelet. It is thought that alloantibodies, which are generated in an alloimmune response against platelet alloantigens, interact with the extracellular domains of the alloantigens.

The platelet alloantigens that a person has are determined by the person's genetics. A donor, because of his or her genetics, may have a platelet alloantigen, which a recipient, who receives blood or platelets from the donor, does not have, because of the recipient's genetics. In such a situation, the immune system of the recipient may recognize as "foreign," and raise an immune response against, the platelet alloantigen, which the donor has but the recipient does not.

Membrane glycoprotein alloantigens have been characterized for both human red blood cells and human platelets. It is noteworthy, however, that they also occur on other cell types, such as leucocytes and endothelial cells, where they may also occasion various disorders on account of alloimmune responses.

Recognized classes of red blood cell and platelet alloantigens have been described, over the past 30 years, based on observations of antibody reactions occurring when blood recipients have been exposed to blood from donors.

A recent review of human platelet alloantigen systems is provided by Newman and Goldberger, *Baillière's Clin. Haematol.* 4, 869–888 (1991).

Several "systems" of platelet alloantigens have been characterized which are diallelic. For each of these systems, there are two alloantigens, each of which is provided by one of two alleles of the gene which is associated with the system. Because a gene occurs twice in the normal human genome, a person can be homozygous for one or the other of the alloantigens or heterozygous for the alloantigens in the diallelic systems. The alloantigens occur on glycoprotein molecules which are heterodimers, i.e., they consist, in each case, of one each of two glycoprotein subunits that differ, typically significantly, in amino acid sequence and other characteristics. For each of these diallelic systems which has been characterized at the level of protein and gene sequences, it has been found that the difference in sequence which gives rise to the alloantigen occurs on one of the two subunits of the associated heterodimeric glycoprotein.

One diallelic system of human platelet alloantigens is the $Br^a/Br^b$ diallelic system associated with GPIa/IIa, a membrane glycoprotein "integrin," which occurs on platelets and various cell types, such as leukocytes, fibroblasts and epithelial cells, and each molecule of which consists of one glycoprotein subunit designated "GPIa" and one glycoprotein subunit designated "GPIIa." Kiefel et al., *Blood* 733: 2219–2223 (1989); Santoso at al., *Br. J. Haematol.* 72: 191–98 (1989). GPIa/IIa, which is also known as "integrin $\alpha_2\beta_1$," or "VLA-2,", is the collagen receptor on platelets and other cell types (e.g., lung fibroblasts). In unstimulated platelets, GPIa/IIa mediates $Mg^{2+}$-dependent platelet adhesion to collagen. Staatz et al., *J. Cell. Biol.* 108:1917–24 (1989). Br alloantigens have also been found on activated T lymphocytes (Santoso et al., *Hum. Immunol.* 24:237–46 (1989)) and endothelial cells (Giltay et al., *Br. J. Haematol.* 75:557–600 (1990)), which is consistent with the tissue distribution known for integrin $\alpha_2\beta_1$.

The frequencies for the Br alleles are 0.1110 for $Br^a$ and 0.8890 for $Br^b$ in the caucasian population. Thus, in this population, 19.8% are heterozygous for the alleles, and will not mount an alloimmune response due to Br incompatibility (not possessing a Br alloantigen on platelets received from another); 1.2% are homozygous for the $Br^a$ allele and may mount an immune response due to Br alloantigen incompatibility against platelets received from anyone in the 98.8% of the caucasian population that is not homozygous for the $Br^a$ allele; and 79.0% are homozygous for the $Br^b$ allele and may mount an immune response due to Br alloantigen incompatibility against platelets received from anyone in the 21.0% of the caucasian population that is not homozygous for the $Br^b$ allele.

As indicated above, alloimmunization based on Br incompatibility (i.e., introducing into the blood stream of a recipient platelets with a Br alloantigen which the recipient does not have) can result in bleeding disorders due to platelet destruction, such as NATP (Kiefel et al., *Vox Sang.* 54:101–06 (1987); Kiefel et al., *Vox Sang.* 60:244–45 (1991); Bettaieb et al., *Vox Sang.* 60:230–34 (1991), PTP (Christie et al., *Blood* 77:2785–89 (1991) and PTPR (Bierling et al., *Br. J. Haematol.* 73:428–29 (1989)). The location, in the GPIa/IIa molecule, or the nature of the polymorphism which underlies the $Br^a/Br^b$ alloantigen system, and the genetic polymorphism, which underlies the polymorphism at the glycoprotein level, have not heretofore been known, although there has been speculation (Newman and Goldberger, supra) that the polymorphism resides on the GPIa subunit alone.

Furthermore, heretofore it has not been possible to obtain non-human antibody (polyclonal or monoclonal), as from a rat, mouse, goat, chicken, or the like, with specificity for the $Br^a$ alloantigen but not the $Br^b$ alloantigen or vice-versa sufficient for use of the antibody, in an immunoassay, for typing for Br phenotype using platelets or GPIa/IIa molecules.

The complete amino acid sequence of the GPIa portion of a GPIa/IIa complex has been deduced from the nucleotide sequence of the corresponding cDNA obtained from an human lung fibroblast cDNA library. Takada and Hemler, *J. Cell Biol.* 109: 397–407 (1989). The mature GPIa polypeptide has 1152 amino acids with, in lung fibroblasts, an extracellular domain that is said to have 1103 amino acids, a transmembrane domain, and a short cytoplasmic domain that is said to have 22 amino acids. Although the overall sequence homology between GPIa (an integrin $\alpha^2$ subunit) and other integrin $\alpha$ subunits is only 18–25%, GPIa has a similar distribution of cysteine residues and cation-binding domains with these other subunits. GPIa also contains a 191 amino acid insert, called the "I-domain," which contains potential sites for interaction with collagen.

Previously developed technology, involving target nucleic acid amplification starting with platelet RNA and sequencing of the resulting amplified nucleic acid, has been applied with the currently recognized diallelic platelet alloantigen systems, other than the $Br^a/Br^b$ system, to determine, at the nucleotide sequence level, the base differences and, at the amino acid sequence level, the amino acid differences between the two alleles of each system. Newman and Aster, U.S. Pat. No. 5,091,302; Newman et al., *J. Clin. Invest.* 82,739–744 (1988); Newman et al., *J. Clin. Invest.* 83, 1778–1781 (1989)($Pl^A$ system); Lyman et al., *Blood* 75, 2343–2348 (1990) (Bak system); Kuipers et al., *J. Clin. Invest.* 89, 381–384 (1992)(Ko system); Wang et al., *J. Clin. Invest.* 90, 2038–2043 (1992)(Pen system). In each of the $Pl^A$, Bak, Ko and Pen systems, it has been found that an amino acid difference at a single position differentiates the subunits, that differ in amino acid sequence, in the two alleles and that a nucleotide difference at a single position differentiates the coding regions of the mRNAs (and presumably the genes) that encode these subunits.

SUMMARY OF THE INVENTION

We have now discovered that a single amino acid difference in the GPIa membrane glycoprotein distinguishes the $Br^a$ and $Br^b$ allelic forms. This difference is at amino acid position 505 of the mature, 1152 amino acid GPIa. The amino acid at this position is Lys in the $Br^a$ allele and Glu in the $Br^b$ allele.

Further, we have discovered that this difference in amino acid sequence between the allelic forms of GPIa is due to a single base substitution, from adenine in the $Br^a$ allele to guanine in the $Br^b$ allele, at the nucleotide at the 5'-end of the codon which codes for the amino acid at position 505 in the in the mature GPIa subunit. The position, in the nucleotide sequence of the mRNA encoding the GPIa or the corresponding coding strand of the cDNA corresponding to this mRNA, at which the difference in base between the Br_a-encoding polymorph and Br_b-encoding polymorph occurs, is position 1648, as shown in the sequence at FIG. 2 of Takada and Hemler, supra, which is incorporated herein by reference.

This is position 1600 in SEQ ID NO:1. SEQ ID NO:1 is the cDNA sequence corresponding to the 1181 amino acids of the GPIa precursor (and the translation stop codon at the 3'-end) for the $Br^b$ allele. In the $Br^a$ allele form, G occurs at position 1600, rather than A. The ATG at the 5'-end of the sequence in SEQ ID NO:1 corresponds to the translation start for the precursor form (with leader peptide) of GPIa. The triplet corresponding to the N-terminal amino acid of the mature protein is at positions 88–90 in SEQ ID NO:1.

In view of this discovery, it will be readily apparent to the skilled what the present invention provides.

Based on the discovery, the present invention provides oligonucleotides and polynucleotides, including (but not limited to) probes which can be used to determine whether a person is homozygous for one or the other of the Br alleles or heterozygous for these alleles and to type individuals for their Br phenotype (i.e., the Br alloantigen(s) which they have). Further, the invention provides methods of using such oligonucleotides, and test kits to facilitate their use, in such determinations and typing. These oligonucleotides of the invention will be capable of distinguishing whether, in the gene or the mRNA for the GPIa, the base at the 5'-terminus of the triplet (in the coding strand of the gene) or the codon (in the mRNA) which corresponds to the amino acid at position 505 in the sequence of the mature GPIa is adenine or guanine. These probes will typically be DNAs, but may be RNAs, and may be labelled for detection, as understood in the nucleic acid probe hybridization assay art.

For example, an oligonucleotide of the invention may be converted to a probe by being end-labeled using digoxigenin-11-deoxyuridine triphosphate. Such probes may be detected immunologically using alkaline-phosphate-conjugated polyclonal sheep antidigoxigenin $F_{ab}$ fragments and nitro blue tetrazolium with 5-bromo-4-chloro-3-indoyl phosphate as chromogenic substrate. See MacFarland et al., *Blood* 78, 2276–2282 (1991); Ziacher et al., *Nucl. Acids Res.* 17, 4411 (1989).

Still further, based on the discovery, which underlies the invention, of the molecular basis for the $Br^a/Br^b$ alloantigen system, the invention provides non-human polyclonal and monoclonal antibodies, which can be used to distinguish one Br allelic form of GPIa from the other, whether the GPIa is part of the GPIa/GPIIa complex embedded in or isolated from a membrane or is isolated. These antibodies of the invention, which are preferably provided in an aqueous buffer solution, and the immunoassays of the invention which employ such antibodies, are useful for determining whether a person has one or both of the Br alloantigens and for typing individuals for their Br phenotype. Methods of using the antibodies of the invention in the immunoassays of the invention and in such determinations are also encompassed by the invention. The invention also provides test kits to facilitate carrying out such immunoassays and determinations.

Again, based on the discovery which underlies the invention, of the molecular basis for the Br$^a$/Br$^b$ alloantigen system, the invention provides peptides or polypeptides which are useful for various purposes. These peptides or polypeptides are typically between 4 and 100, and more typically between 7 and 50, amino acids in length and have amino acid sequences that are the same as those of segments, of the sequences for GPIa, that include the amino acid at position 505 of the mature GPIa. This is the amino acid corresponding to the triplet at positions 1600–1602 in the sequence presented in SEQ ID NO:1 or the corresponding sequence for the cDNA for the GPIa with the Br$^b$ allelic form.

These peptides or polypeptides are useful as antigens (usually coupled to a larger, immunogenic carrier (proteinaceous or otherwise), as known in the art) for making the polyclonal or monoclonal antibodies of the invention. The peptides or polypeptides are also useful in screening monoclonal antibody-producing cultures (hybridoma cultures/*E. coli* cultures (Science 246, 1250–1251(1989)) for those that produce monoclonal antibodies of the invention.

The invention also encompasses immunogenic compositions which comprise a peptide or polypeptide of the invention and which are immunogenic in a bird, including, without limitation, a chicken, or a mammal, including, without limitation, a mouse, rat, goat, rabbit, guinea pig, sheep or human, and which consist of an immunogenicity-imparting "carrier" which may be but is not necessarily a protein as known in the art that is immunogenic in a bird or mammal, coupled to at least one peptide or polypeptide of the invention, which has an amino acid sequence that is the same as that of a segment, of the sequence for GPIa, that includes the amino acid at position 505 of the mature subunit.

The present inventions also provides methods of using the peptides, polypeptides and immunogenic compositions of the invention for making antibodies of the invention, and methods of using the peptides and polypeptides of the invention in screening monoclonal antibody-producing hybridoma cultures for those that produce monoclonal antibodies of the invention.

These peptides or polypeptides, as well as antibodies, which are specific for the Br$^a$ or Br$^b$, but not both, allelic forms of GPIa in platelet membranes and can be produced by a mammal (including an human) immunized with the peptides or polypeptides, which themselves happen to be immunogenic, or the immunogenic compositions of the invention, are also useful therapeutically. The invention also provides the methods of using the peptides and polypeptides of the invention, and antibodies made using the ones that are immunogenic and the immunogenic compositions of the invention, in therapeutic applications. Administration to a person, who is suffering from, or at risk for, for example, PTP or PTPR, or a mother at risk for passing NATP-causing alloantibodies to her fetus, of one of the peptides or polypeptides, that would be bound by the anti-Br alloantibodies in such a person, would inhibit the binding of the alloantibodies to the person's (or the fetus' platelets and thereby inhibit the platelet destruction and abnormal bleeding associated with the disorders. Alternatively, administration to such a person of antibodies (particularly human antibodies), which are produced using a peptide or polypeptide of the invention, which is immunogenic by itself, or an immunogenic composition of the invention, and which are specific for the Br allelic form of the GPIa on the person's platelets which is associated with the PTP or PTPR, from which the person is suffering or may suffer, would induce the production of anti-idiotypic antibodies, which, in turn, would inhibit the platelet-destructive effects of the anti-Br alloantibodies, which are generated by the person's own immune system and which were causing or threatening to cause the PTP, PTPR or NATP. These therapeutic applications of peptides and polypeptides of the invention would be especially useful in treating NATP in a newborn, because the alloantibody giving rise to NATP in the newborn is not continuously produced by the immune system of the newborn but is acquired passively, and therefore in limited, non-replenished quantity, by the newborn from its mother.

Thus, in accordance with one aspect of the present invention, a nucleic acid probe molecule is provided that hybridizes to a portion of the GPIa gene, or a portion of GPIa-encoding mRNA or cDNA prepared from such mRNA, which portion includes a nucleotide corresponding to the 5'-nucleotide of the codon for the amino acid at position 505 of the mature GPIa subunit, and that is capable of distinguishing one Br allele from the other through the ability to hybridize under stringent conditions to the portion in question only when the nucleotide in question is A (or dA), when the probe is to detect the Br$^a$ allele, or G (or dG), when the probe is to detect the Br$^b$ allele. The nucleotide in question is at position 1648 of the GPIa cDNA sequence provided by Takada and Hemler, supra, and at position 1600 in SEQ ID NO:1. The cDNA sequence presented by Takada and Hemler has A at this position, and so is the sequence corresponding to the Br$^a$ allele. Similarly, SEQ ID NO:1 is the sequence of a segment of the cDNA encoding the GPIa corresponding to the Br$^a$ allele. A probe of the invention may be an RNA or a DNA, although preferably it is a DNA. It will preferably be prepared by in vitro, chemical synthesis, and, to provide the desired specificity, will preferably have about 10–about 30 bases, although, as understood in the nucleic acid probe hybridization assay art, as few as 8 and as many as about 50 bases may be useful, depending on the position, within the probe, where the potential mismatch with the target is located, the extent to which a label on the probe might interfere with hybridization, and the physical conditions (e.g., temperature, pH, ionic strength) under which the hybridization of probe with target is carried out. Reference may be had to SEQ ID NO:1 or SEQ ID NO: 8–10 (for genomic sequencing) or Takada and Hemler, supra, for possible sequences of probes in accordance with the invention.

In accordance with another aspect of the present invention, a test kit for Br alloantigen typing is provided comprising:

(a) means for amplifying nucleic acid that comprises at least a portion of a GPIa gene, a GPIa-encoding mRNA, or a GPIa cDNA made from such RNA, wherein the portion includes a nucleotide (e.g., the one at position 1600 in SEQ ID NO:1) corresponding to the 5'-nucleotide of the codon for the amino acid at position 505 of the mature GPIa subunit, and (b) an oligonucleotide probe of the invention, that distinguishes one Br allele from the other. The "means for amplifying" will, as the skilled will readily understand, depend on the amplification method to be used. Thus, for example, these means might include suitable primers, a suitable DNA polymerase, and the four 2'-deoxyribonucleoside triphosphates (dA, dC, dG, dT), if amplification is to be by the PCR method. To cite another example, if the amplification is to be by a method relying on transcription, such as the 3SR method, the means will include two primers, at least one of which, when made double-stranded, will provide a promoter, an RNA polymerase capable of transcribing from that promoter, a reverse transcriptase to function in primer-initiated, DNA-directed and RNA-directed, DNA polymerization and possibly also (as in the case of 3SR) in RNAse H degradation of RNA to free DNA strands from RNA/RNA hybrids, the four ribonucleoside triphosphates (A, C, G and U), and the four 2'-deoxyribonucleoside triphosphates. In another example, if the amplification is by the ligase chain reaction, the means will include two oligonucleotides (DNAs) and a suitable DNA ligase that will join the two if a target, to which both can hybridize adjacent one another in ligatable orientation, is present.

The oligonucleotide probe of the invention will be labeled. The label may be any of the various labels available in the art for such probes, including, but not limited to, $^{32}$P; $^{35}$S; biotin, to which a signal generating moiety, bound to or complexed with avidin, can be complexed; a fluorescent moiety; an enzyme such as alkaline phosphatase which is capable of catalyzing a chromogenic reaction; digoxigenin, as described above, or the like.

As indicated in the examples, RFLP analysis can be employed, using MnlI or isoscizomers thereof, in analyzing cDNA or genomic DNA (with or without amplification) to determine Br genotype.

In accordance with a further aspect of the present invention, a test kit for Br alloantigen typing is provided comprising a non-human antibody that distinguishes the two allelic forms of GPIa. The antibody of a kit may be polyclonal or, preferably, monoclonal and, in addition to its specificity for either but not both Br alloantigens (on the surface of platelets or separated therefrom) or the GPIa subunit of one but not both of such alloantigens, typically will recognize a polypeptide molecule encoded by a nucleotide sequence encoding at least amino acid 505 of a GPIa polypeptide (the amino acid at the position corresponding to bases 1600–1602 in SEQ ID NO:1).

There has also been provided, in accordance with another aspect of the present invention, a method of typing for Br allele, comprising the steps of (A) obtaining, by a target nucleic acid amplification process applied to mRNA from human platelets, an assayable quantity of amplified nucleic acid with a sequence that (i) is that of a subsequence (or the complement of a subsequence) of the mRNA that encodes a GPIa said subsequence including the nucleotide at the position in the mRNA corresponding to position 1600 in SEQ ID NO:1 and (B) analyzing (e.g., in a nucleic acid probe hybridization assay employing an oligonucleotide probe or probes according to the invention) the amplified nucleic acid obtained in step (A) to determine the base or bases at the position in the amplified nucleic acid that corresponds to position 1600 in SEQ ID NO:1. It is noteworthy that, if the product of the amplification is double-stranded DNA, analysis for Br phenotype can be carried out by a RFLP (restriction fragment length polymorphism) analysis comprising exposing the amplified DNA to the restriction endonuclease MnlI under conditions whereby the DNA will be cleaved if it includes a site for cleavage by that enzyme. Such DNA, prepared from mRNA encoding the Br$^b$ alloantigen, because that RNA has a G rather than an A at the position corresponding to nucleotide 1600 in SEQ ID NO:1, includes a recognition site for that endonuclease that such DNA, prepared from mRNA encoding the Br$^a$ alloantigen, does not. If the analysis, by whatever method, of the amplified nucleic acid reveals that there is only an A (or dA) at the position corresponding to position 1600, the platelets (and blood from which they came) have only the Br$^a$ alloantigen and the individual, from whom the platelets came, is homozygous for Br$^a$. Alternatively, if the analysis of the amplified nucleic acid reveals that there is only a G (or dG) at the position corresponding to position 1600, the platelets (and blood from which they came) have only the Br$^b$ alloantigen and the individual, from whom the platelets came, is homozygous for Br$^b$. Finally, if the analysis indicates that there is either an A (or dA) or a G (or dG) at that position, the platelets (and blood from which they came) have both Br alloantigens and the individual, from whom the platelets came, is heterozygous for Br alloantigen.

In one application of the typing methods of the invention, they are applied to two individuals to determine whether blood or platelets from one would provoke an alloimmune response, and possibly PTP or PTPR, in the other. The typing method can be applied with a man and a woman, who are contemplating conceiving or have conceived a child together, to determine the risk that the child would be at risk for NATP and the woman would be at increased risk for PTP or PTPR. If the woman is heterozygous for Br alloantigen, there would be, due to Br alloantigen incompatibility, no risk of NATP and no increased risk for the woman of PTP or PTPR. If the woman is homozygous for one of the Br alloantigens, there would be, due to Br alloantigen incompatibility, risk of NATP in a child and increased risk of PTP or PTPR for the woman unless the man is homozygous for the same Br alloantigen as the woman.

In accordance with yet another aspect of the present invention, a method of typing an individual for Br alloantigen is provided that comprises analyzing the genomic DNA of the individual to determine the Br alloantigen(s) of the individual. Applications of this method are substantially the same as those of the method of the invention for typing for Br alloantigen that begins with platelet mRNA.

This method of the invention, entailing analysis of genomic DNA, can be carried out in substantially the same way as outlined above for analysis of mRNA, namely, first amplifying the genomic DNA and then analyzing to product of the amplification to ascertain whether there is only dA, only dG, or both dA and dG, at the position in the coding strand of the genomic DNA corresponding to position 1600 in SEQ ID NO:1. Other features and advantages of the present invention will become apparent from the following detailed description.

DETAILED DESCRIPTION OF THE INVENTION

Standard abbreviations, as follows, are used herein for the 20 naturally occurring amino acids:

| | |
|---|---|
| L-alanine | Ala |
| L-arginine | Arg |
| L-asparagine | Asn |
| L-aspartic acid | Asp |
| L-cysteine | Cys |
| L-glutamic acid | Glu |
| L-glutamine | Gln |
| glycine | Gly |
| L-histidine | His |
| L-isoleucine | Ile |
| L-leucine | Leu |
| L-lysine | Lys |
| L-methionine | Met |
| L-phenylalanine | Phe |
| L-proline | Pro |
| L-serine | Ser |
| L-threonine | Thr |
| L-tryptophan | Trp |
| L-tyrosine | Tyr |
| L-valine | Val |

The standard, one-letter codes "A," "C," "G," and "T" are used herein for the nucleotides adenylate, cytidylate, guanylate, and thymidylate, respectively. The skilled will understand that, in DNAs, the nucleotides are 2'-deoxyribonucleotide-5'-phosphates (or, at the 5'-end, possibly triphosphates) while, in RNAs, the nucleotides are ribonucleotide-5'-phosphates (or, at the 5'-end, possibly triphosphates) and uridylate (U) occurs in place of T. "N" means any one of the four nucleotides. On occasion herein, dA, dC, dG and dT might be used for the respective 2'-deoxyribonucleotides.

Unless otherwise specified or required by the context, "nucleic acid" means DNA or RNA and "nucleotide" means ribonucleotide or 2'-deoxyribonucleotide.

Reference herein to a "mature" GPIa subunit means, in the case of the GPIa subunit of the GPIa/IIa complex, the 1152-amino acid-long polypeptide, for which the amino acid sequence, deduced from a cDNA sequence, is provided in Takada and Hemler, supra, and which is denoted by them as the mature subunit (i.e., thought to be the subunit after cleavage of any leader peptide). This subunit, of the Br$^a$ alloantigen, may be referred to herein as [Lys$^{505}$] GPIa. In the case of the GPIa subunit of the Br$^b$ alloantigen, reference herein to the "mature" subunit means the 1152-amino-acid long polypeptide with the same sequence as [Lys$^{505}$] GPIa except for the presence of Glu, in place of Lys, at amino acid position 505. Thus, the GPIa subunit of the Br$^b$ subunit, may be referred to herein as [Glu$^{505}$]GPIa.

It has been determined that a single nucleotide of the GPIa gene is responsible for the Br polymorphism in GPIa/IIa. Characterization of GPIa/IIa, and thereby of the Br$^a$ and Br$^b$ alleles, was undertaken by acid-mediated disassociation of GPIa/IIa followed by immunoprecipitation with anti-Br$^a$ and anti-Br$^b$ alloantibodies. This immunoprecipitation yielded GPIa free of GPIIa, which demonstrates that the polymorphism underlying the Br system resides solely on the GPIa subunit of GPIa/IIa. Removal of sialic acid residues from GPIa did not affect the binding the anti-Br$^a$ and anti-Br$^b$ antibodies to molecules of the appropriate phenotype, which indicates that carbohydrate residues are not involved in the formation of Br antigenic epitopes.

Further characterization of the two alleles was undertaken using platelet RNA in the polymerase chain reaction ("PCR"). Platelet mRNA transcripts were obtained from serologically-defined Br$^{a/a}$, Br$^{a/b}$ and Br$^{b/b}$ individuals. An analysis of a 414 bp fragment encompassing nucleotide 1486–1900 revealed a single A⇌G polymorphism at base 1648. This single nucleotide polymorphism results in a MnlI restriction site in Br$^b$ that is not present in Br$^a$. On the basis of this MnlI site, Br$^a$ can be distinguished from Br$^b$ by restriction fragment length polymorphism ("RFLP"). The single nucleotide polymorphism also results in an amino acid Lys⇌Glu polymorphism at residue 505 of the mature GPIa polypeptide chain. This amino acid polymorphism is located between the first and second divalent cation-binding domains of GPIa. Additionally, this polymorphism is believed to impart local changes in the conformation of GPIa due, at least in part, to the reversal of electrical charge. The polymorphism, however, does not cause differences in the ability Br$^a$ and Br$^b$ homozygous platelets to adhere to collagen types I, III and V. Additionally, the binding of anti-Br$^a$ and anti-Br$^b$ antibodies to the appropriate phenotype did not interfere with platelet adhesion to any of the above collagen types. Accordingly, the Lys⇌Glu polymorphism at position 505 of the GPIa polypeptide affects the formation of Br alloantigen epitopes, but does not impair platelet function.

Identification and characterization of the Br alloantigen system permits pre- and post-natal diagnosis of the Br phenotype of an individual, which provides a warning for the possibility of NATP, PTP and PTPR. Allelic Br typing of GPIa equates with the Br status of the GPIa/IIa complex of an individual. Moreover, the elucidation of the Br system will permit the development of therapeutic strategies to avoid or control diseases that result from Br incompatibility. The present invention can be applied to these tasks and goals in a variety of ways, illustrative examples of which are discussed below.

For example, an oligonucleotide probe can be synthesized, in accordance with the present invention, that will hybridize to a cDNA segment, derived from GPIa mRNA, that contains the base guanine at polymorphic nucleotide 1648. (nucleotide=guanylate). Alternatively, an oligonucleotide probe can be synthesized that will hybridize with a GPIa cDNA segment containing the base adenine at nucleotide 1648. (nucleotide=adenylate). These allele-specific probes can be appropriately labeled and added to the generated cDNA segments under annealing conditions, such that one of the allelespecific probes hybridizes and can be detected, thereby identifying the specific Br$^a$ or Br$^b$ allele. In accordance with conventional procedures, the design of an oligonucleotide probe according to the present invention preferably involves adjusting probe length to accommodate hybridization conditions (temperature, ionic strength, exposure time) while assuring allele-specificity. A length of ten to thirty nucleotides is typical.

Diagnostic kits can also be used, in accordance with the present invention, for the determination and diagnosis of alloantigen phenotypes via the procedures described herein. Such a kit can include, inter alia, antibodies or antibody fragments to an antigenic determinant expressed by either of the above-described Br$^a$- and Br$^b$-encoding sequences. These antibodies would react with the blood sample of an individual so as to indicate whether that individual has a Br$^a$ or Br$^b$ phenotype. Alternatively, all the reagents required for the detection of nucleotide(s) that distinguish the Br alloantigens, by means described herein, can be provided in a single kit that uses isolated genomic DNA, platelet mRNA or corresponding cDNA from an individual. A kit containing a labeled probe that distinguishes, for example, nucleotide 1648 of GPIa can be utilized for Br alloantigen phenotyping.

A further beneficial use of the nucleotide sequences that distinguish the Br$^a$ allele from the Br$^b$ allele is to obtain or synthesize the respective expression product, in the form of a polypeptide, encoded by these nucleotide sequences. These polypeptides can be used to generate antibodies for diagnostic and therapeutic uses, for example, with regard to pathological conditions such as PTP, PTPR or NATP.

A polypeptide within the present invention which can be used for the purpose of generating such antibodies preferably comprises an amino-acid sequence that corresponds to (i.e., is coincident with or functionally equivalent to) a fragment of the GPIa molecule that includes amino acid 505. When amino acid 505 is lysine, the polypeptide can be used, as described above, to produce antibodies that specifically bind the Br$^a$ form of GPIa; when it is glutamic acid, antibodies can be obtained that particularly recognize the Br$^b$ form. The class of polypeptides thus defined, in accordance with the present invention, is not intended to include the native GPIa molecule or native GPIa/IIa complex, but does encompass fragments of the molecule or complex as well as synthetic polypeptides meeting the aforementioned definition.

Although the length of a polypeptide within this class is not critical, the requirement for immunogenicity may require that the polypeptide be attached to a immunogenicity-imparting carrier. Such carriers include a particulate carrier like a liposome or a soluble macromolecule (protein or polysaccharide) with a molecular weight in the range of about 10,000 to 1,000,000. Additionally, it may be desirable to administer the polypeptide with an adjuvant, such as complete Freund's adjuvant. For artificial polypeptides, as distinguished from GPIa fragments, maximum length is determined largely by the limits of techniques available for peptide synthesis, which are currently about fifty amino acids. Thus, a synthetic polypeptide of the present invention is preferably between four to about fifty amino acids in length.

In the context of the present invention, the term "antibody" encompasses monoclonal and polyclonal antibodies produced by any available means. Such antibodies can belong to any antibody class (IgG, IgM, IgA, etc.) and may be chimeric. The term "antibody" also encompasses fragments, like Fab and $F(ab')_2$, of anti-$Br^a$ or anti-$Br^b$ antibodies, conjugates of such fragments, and so-called "antigen binding proteins" (single-chain antibodies) which are based on anti-$Br^a$ or anti-$Br^b$ antibodies, in accordance, for example, with U.S. Pat. No. 4,704,692, the contents of which are hereby incorporated by reference. Human alloantisera currently used for serological typing are specifically excluded from this definition. Alternatively, monoclonal antibodies or fragments thereof within the present invention can be produced using conventional procedures via the expression of isolated DNA that codes for variable regions of such an Mab in host cells like *E. coli* (see, e.g., Ward et al., *Nature*, 341:544–546 (1989)) or transfected murine myeloma cells (see Gillies et al., *Biotechnol.* 7:799–804 (1989); Nakatani et al., *Biotechnol.* 7:805–810 (1989)).

Diagnostic applications of these antibodies are exemplified, according to the present invention, by the use of a kit containing an anti-$Br^a$ or an anti-$Br^b$ antibody, which undergoes a reaction with a sample of an individual's blood to determine a $Br^a$ or $Br^b$ platelet phenotype. Such a reaction involves the binding of anti-$Br^a$ antibody to $Br^a$ antigen or the binding of anti-$Br^b$ antibody to $Br^b$ antigen. The observation of antibody-antigen complex in a blood sample would indicate a positive result. A kit of this type could be used to diagnose, or to help prevent, the occurrence of pathological conditions like PTP, PTPR, or NATP.

A polypeptide of the present invention that is recognized specifically by anti-$Br^a$ or anti-$Br^b$ antibodies can be used therapeutically. Thus, antibodies raised against such a polypeptide can employed in the generation, via conventional methods, of anti-idiotypic antibodies, that is, antibodies that bind an anti-$Br^a$ or anti-$Br^b$ antibody. See, e.g., U.S. Pat. No. 4,699,880, the contents of which are hereby incorporated by reference. Such anti-idiotypic antibodies would bind endogenous or foreign anti-Br antibodies in the blood of an individual, which would treat or prevent pathological conditions associated with an immune response to a "foreign" Br alloantigen. Alternatively, a polypeptide within the present invention can be administered, with a physiologically-compatible carrier, to achieve the same qualitative effect, namely, the selective reduction or elimination of circulating anti-Br antibodies from a patient suffering or at risk from an immune response.

The present invention is further described below by reference to the following, illustrative examples.

EXAMPLE 1 Localization of Br Antigenic Determinants to the

GPIa Subunit

In order to localize the epitope of the Br alloantigens, the GPIa/IIa complex was disassociated by treating the human fibroblast lysates containing the complex with an acidic buffer according to Gullberg et al., *Exp. Cell Res.* 186: 264–72. First, approximately $10^9$ $I^{125}$-labeled platelets were solubilized in 1 ml of 10 mM tris buffer, pH 8.0, containing 1% NP40, 1% leupetin (Sigma, Munich, Germany) at 4° C. for 30 minutes. After centrifugation at 13,000×g for 30 minutes at 4° C. platelet lysates were precleared on a gyrorotator overnight with 100 µl of Sepharose-4B® beads (Pharmacia, Freiburg, Germany) coupled with rabbit anti-human IgG (Dako, Hamburg, Germany). Aliquots of 500 µl precleared platelet lysates were acidified with citrate buffer to pH 2.0 for 30 minutes at 4° C. After neutralization with 1M Tris buffer, pH 8.0, lysates were immediately adsorbed with monoclonal antibody K20 (Dianova of Hamburg, Germany) coupled to Sepharose-4B beads to remove any remaining GPIa/IIa complex that had not dissociated. GPIa was subsequently immunoprecipitated with anti-$Br^a$ anti-Brb platelet-specific human alloantibodies coupled to Sepharose-4B beads. After incubation for 30 minutes at 4° C., the beads were washed three times with 10 mM Tris buffer, pH 8.0, containing 0.1% NP40. The pellet was resuspended in 100 µl sample buffer containing 2% sodium dodecyl sulfate ("SDS") and boiled for 5 minutes. The immunoprecipitated proteins were electrophoresed on a 7.5% SDS-polyacrylamide gel. Finally, the gels were dried and autoradiographed on Kodak X-Omat S film using an intensifying screen (Cronex Hi-Plus; Dupont, Frankfurt, Germany).

The alloantibodies specific to $Br^a$ and $Br^b$ were obtained from mothers of children with NATP and from polytransfused patients. The Br phenotypes of donors were determined by the MAIPA glycospecific immunoassay described in Kiefel et al., *Blood* 70:1222–26 (1987).

This procedure precipitated GPIa without coprecipitating GPIIa. Because the anti-$Br^a$ and anti-$Br^b$ precipitating GPIIa. alloantibodies bound dissociated GPIa, it could be concluded that the Br antigenic determinants are carried on GPIa itself, rather than being present only in the GPIa/IIa complex.

EXAMPLE 2: Characterization of Br Antigenic Determinants

In order to determine the biochemical characteristics of the Br epitopes, lysates from untreated and neuraminidase-treated, $^{125}$I-labeled platelets were immunoprecipitated. Platelets were labeled with using the lactoperoxidase catalyzed method of Phillips et al., *J. Biol. Chem.* 252: 2121–26 (1977). The neuraminidase removes sialic acid residues from proteins such as the GPIa/IIa complex.

Labeled platelets were then immunoprecipitated with human anti-$Br^a$ serum. See Santoso et al., *Br. J. Haematol.* 72: 191–98(1989). Based on SDS-polyacrylamide gel electrophoresis, anti-$Br^a$antibodies precipitated desialylated GPIa/IIa, which had a molecular weight that was lower than that of native GPIa/IIa. This result suggested that the Br epitope does not depend on glycosylation.

To confirm this hypothesis, different $Br^a$-, $Br^b$- and also $Bak^a$-antisera (control) were adsorbed with untreated and neuraminidase-treated phenotyped platelets. First, aliquots of $8 \times 10^7$ washed platelets in phosphate buffered saline ("PBS") buffer, pH 6.2, supplemented with 2% bovine serum albumin ("BSA") were incubated in the absence or presence of 40 microunits protease-free neuraminidase from Arthrobacter ureafaciens (Boehringer Mannheim, Germany) for 6 hours at 37° C. and washed twice with PBS. Seventy microliters of diluted sera containing anti-$Br^a$, anti-$Br^b$, or anti-$Bak^a$ were adsorbed twice with $4 \times 10^5$ untreated or neuraminidase-treated platelets for 30 minutes at 37° C. After centrifugation (13,000×g for 3 minutes), the remaining specific alloantibodies in the supernatants were tested in the MAIPA assay using monoclonal antibodies Gi14 (anti GPIa/IIa) or Gi5 (anti GPIIb/IIIa) as capture antibodies as described in Kiefel et al., Blood 70:1222–26 (1987). The results were expressed as percent adsorption of specific antibody calculated in the following manner:

$$\text{Absorption}(\%) = \frac{(1 - OD_{test} - OD_{blank})}{OD_{max} - OD_{blank}} \times 100\%, \text{ where}$$

$OD_{test}$: diluted sera preabsorbed with neuraminidase-treated or-untreated platelets; $OD_{max}$: diluted sera without preabsorption; $OD_{blank}$: antibody sera without preabsorption.

The amount of specific alloantibodies remaining in the supernatants were then analyzed in a MAIPA assay. The results were calculated as percent adsorption as shown in Table 1. All 18 Br antibodies were equally adsorbed with untreated and neuraminidase-treated platelets. In contrast, the $Bak^a$ antibodies were adsorbed by untreated platelets, but not by neuraminidase-treated platelets (83.3% vs. 10.4% absorption). This implies that $Bak^a$ epitopes, unlike Br epitopes, are influenced by neuraminidase treatment, which confirms earlier reports. Take et al., Br. J. Haematol. 76: 395–400 (1990); Goldberger et al., Blood 78:681–87 (1991). More importantly, however, these results confirm that the Br epitopes are independent of glycosylation.

TABLE 1

| Alloantibodies | Absorption (%) | | n |
|---|---|---|---|
| | untreated | N-treated | |
| $Br^a$ | 88.5 + 11.8 | 89.7 + 10.2 | 5 |
| $Br^b$ | 78.6 + 7.5 | 82.9 + 6.3 | 5 |
| $Bak^a$ | 93.1 + 11.4 | 93.7 + 5.6 | 3 |
| $Bak^a$ (N+) | 83.3 + 19.7 | 10.4 + 10.0 | 3 |

N+: Neuraminidase sensitive; n: number of sera tested.

EXAMPLE 3: PCR Amplification and Analysis of PCR Products

Platelet messenger RNA was isolated from EDTA anticoagulated blood of $Br^{a/a}$ and $Br^{b/b}$ individuals in the manner described in Lymann et al., Blood 75:2343–48 (1990). First, platelet mRNA in 10 μl aliquots was heated to 68° C. for 10 minutes and quickly cooled on ice water before reverse transcription. The first strand cDNA was then synthesized using 10 μM oligo dT, 40 units RNAsin (Boehringer Mannheim, Germany), 2 mM of each dNTP (dN triphosphate) (Pharmacia, Freiburg, Germany), 500 units of cloned MMLV reverse transcriptase and 5x enzyme buffer (Gibco, Eggenstein, Germany) in a total volume of 30 μl. The cDNA synthesis was carried out at 40° C. for 45 minutes and was stopped by chilling to 0° C.

Overlapping sets of primers were constructed based on the published sequence of VLA-2 (Takada and Hemler, supra) to amplify the entire coding region of platelet GPIa.

The following oligonucleotides were used for PCR to amplify a region encompassing bases 1438–1852 (SEQ ID NO:1): primer #1, 5'-CAATATCACGGTTATTCAGGCT-CACC-3'(nucleotides 1422–1447)(SEQ ID NO:2); primer #2, 5'-CCCATTTAAATCTCCATAGCCATCC-3' (nucleotides 1890–1866)(SEQ ID NO:3); primer #3, 5'-CAGGCT-CACCGAGGTGACCAGATTGGC-3' (nucleotides 1438–1464) (SEQ ID NO:4); and primer #4, 5-AGTACTG-GAGATGGCTCCTA-3' (nucleotides 1852–1833)(SEQ ID NO:5). Oligonucleotide primers 1 and 2 were paired in one PCR amplification reaction, and oligonucleotides 3 and 4 in another.

The first PCR amplification reaction was carried out by mixing 5 μl of cDNA in solution with 5 μl 10x PCR buffer (as supplied by source of the Taq polymerase, Boehringer Mannheim, Germany), 0.3 μM of each primer (#1 and #2) and 175 μM dNTP in a total volume of 50 μl. After heating at 96° C. for 5 minutes, 3 μl Taq polymerase solution (1:10 dilution, contained 1.5 units) (Boehringer Mannheim, Germany) were added at 85° C. and amplification was performed on a DNA thermal cycler (Biometra, Göttingen, Germany) for 15 cycles. Each cycle consisted of denaturation at 93° C. for 55 seconds, annealing at 52° C. for 55 seconds and extension at 72° C. for 95 seconds. In the final cycle the samples were kept at a temperature of 72° C. for 10 minutes and then chilled to 4° C.

Two microliter aliquots of PCR products were amplified again for 30 cycles using nested primers #3 and #4 under the following conditions: denaturation at 93° C. for 55 seconds, annealing at 50° C. for 55 seconds and at 72° C. for 85 seconds.

The PCR-amplified products were analyzed on 1% agarose gels and stained with ethidium bromide. The DNA was then removed from the gel and purified with Geneclean (Dianova, Hamburg, Germany). The purified DNA was subcloned into pcR™ 1000 (ITC, Heidelberg, Germany) and grown up in mass. The inserts were sequenced by the dideoxy chain termination method using Sequenase 2.0 (USB, Bad Homburg, Germany).

In some cases, the amplified cDNA was digested with MnlI restriction endonuclease and electrophoresed in a 4% NuSieve agarose gel with TBE as a buffer (Biozym, Hameln, Germany).

A comparison of the 415 bp sequences (nucleotides 1438–1852 in SEQ ID NO:1) of $Br^{a/a}$ and $Br^{b/b}$ individuals revealed a single nucleotide difference at base 1600 (in SEQ ID NO:1 ). $Br^{a/a}$ individuals have an adenine at this position 1600, whereas $Br^{b/b}$ individuals had a guanine at the same position. This change results in a Lys⇌Glu amino acid polymorphism at residue 505 of the mature GPIa polypeptide chain. This single nucleotide difference also results in a MnlI restriction site in the $Br^b$ that is not present in $Br^a$. Analysis of the other regions of the GPIa mRNA revealed no other nucleotide differences that segregated with Br phenotype (i.e., that could be used to distinguish the $Br^a$ allele from the $Br^b$ allele).

EXAMPLE 4: RFLP Analysis

In order to confirm that the A⇌G polymorphism at position 1600 (SEQ ID NO:1) segregates with the Br phenotype, a RFLP analysis was undertaken with the MnlI restriction endonuclease, which cleaves at the 5'-end of 5'-TATCAAAGAGG-3'(SEQ ID NO:6)(found in the $Br^b$ cDNA, at bases 1593–1603 in SEQ ID NO:1). This enzyme does not cleave at 5'-TATCAAAAAGG-3'(found in $Br^a$-)(bases 1593–1603 in SEQ ID NO:7). Analysis of the 415 bp cDNA fragment PCR-amplified from $Br^a/Br^a$, $Br^a/Br^b$, and $Br^b/Br^b$ individuals and then digested with MnlI yielded the fragments predicted on the basis that the A⇌G polymorphism at position 1600 (SEQ ID NO:1) segregates with the Br phenotype.

EXAMPLE 5: Platelet Function

To determine whether the amino acid difference affects the function of GPIa/IIa, a platelet adhesion study was undertaken in a manner similar to that described in Kunicki et al., *J. Biol. Chem.* 263: 4516–19 (1988). First, platelets were obtained from ACD-anticoagulated blood by differential centrifugation and washed with Ringer's citrate-dextrose buffer ("RCD"). Aliquots of $2 \times 10^9$ washed platelets in isotonic saline were labelled with 400 µCi $^{51}$Cr at room temperature for 30 minutes. Platelets were then washed once with RCD, once with RCD without $Ca^{2+}$ and $Mg^{2+}$, and resuspended in Tyrode buffer ("TB") without $Ca^{2+}$, $Mg^{2+}$ at a final concentration of $2 \times 10^8$ platelets/ml. For adhesion, microtiter wells were coated overnight at 4° C. with 100 µl collagen type I, III, or V (25 µg/ml in PBS, from Sigma, München, Germany). Additional control wells were coated with 100 µl BSA (bovine serum albumin)(5 mg/ml in PBS, from Serva, Heidelberg, Germany). Each well was then washed twice with 200 µl 15% BSA in PBS ("PBS/BSA") and blocked for 90 minutes with PBS/BSA. For adhesion, 100 µl labelled platelets (about $10^7$ platelets) in TB containing 4 mM $MgCl_2$ were added to coated wells and the trays were incubated in a humidified 37° C. $CO_2$ incubator for 90 minutes. Unbound platelets were removed by gentle aspiration onto absorptive pads and by washing of the wells five times with TB. Bound platelets were solubilized twice with 150 µl-2% SDS, and the amount of bound $^{51}$Cr was determined.

Inhibition of adhesion by monoclonal antibodies Gi9 and Gi14 (both of which recognize epitopes specific to the GPIa/IIa complex itself) or by alloantibodies (specific to $Br^a$ or $Br^b$) was tested by prior incubation of platelets with purified antibodies for 1 hour at room temperature. Antibodies Gi9 and Gi14 were produced in the manner outlined in Santoso et al., *Thromb. Haemostas.* 65:678 (1991) (abstract). The results of this experiment are set forth in Table 2.

TABLE 2

| Platelet phenotype | Antibodies | Specificity | Platelets bound ($10^5$) |
| --- | --- | --- | --- |
| $Br^{a/a}$ | none | — | 16.1 + 5.0 |
| $Br^{b/b}$ | none | — | 16.4 + 4.8 |
| $Br^{a/a}$ | anti-$Br^a$ | $Br^a$ | 17.8 + 4.4 |
| $Br^{b/b}$ | anti-$Br^b$ | $Br^b$ | 17.1 + 4.6 |
| $Br^{b/b}$ | human IgG | — | 17.4 + 4.7 |
| $Br^{b/b}$ | mab Gi14 | GPIa/IIa | 16.8 + 4.2 |
|  | mab Gi9 | GPIa/IIa | 0.3 + 0.3 |

The variance of triplicate did not exceed 5%. The number of platelets adherent to wells coated with BSA was routinely less than 1% of that observed in collagen coated wells. Three donors were tested.

The platelet adhesion of $Br^{a/a}$ platelets was indistinguishable from $Br^{b/b}$ platelets, which shows that the polymorphism (in this context, the amino acid difference) does not affect the adhesion function. Additionally, neither anti-$Br^a$ nor anti-$Br^b$ human alloantibodies inhibited platelet adhesion to Type I collagen, which suggests that the polymorphism is not at a site where GPIa/IIa interacts with collagen. Monoclonal antibody Gi9, directed against a functional epitope of GPIa/IIa, completely inhibited platelet adhesion. Monoclonal antibody Gi14, directed against a different epitope of GPIa/IIa, did not inhibit platelet adhesion. Similar results were obtained when using Type III and Type V collagens.

EXAMPLE 6: Analysis of Genomic DNA

Genomic DNA was isolated from human peripheral blood leukocytes from sodium-EDTA anticoagulated blood by standard proteinase K treatment followed by salting out of protein with supersaturated NaCl, precipitation of the DNA with absolute ethanol, and spooling. Miller et al., *Nucl. Acids Res.* 16:1215 (1988). Segments of the DNA were then PCR-amplified using various sets of primers known to hybridize to GPIa-encoding cDNA in order to determine the genomic DNA sequence around the site of the nucleotide which differs in the $Br^a$ and $Br^b$ alleles. Knowledge of the genomic DNA sequence would permit the use of genomic DNA, in place of cDNA prepared from mRNA, in Br genotyping.

Sequences of genomic DNA around the site of the nucleotide which differs in the Br alleles of the GPIa gene are given in SEQ ID NO:8, SEQ ID NO:9, and SEQ ID NO:10. The site of this nucleotide is position 155 in SEQ ID NO:9. The nucleotide at this position is A for the $Br^a$ allele and G for the $Br^b$ allele.

In SEQ ID NO:8, bases 1–37 correspond to bases 1422–1458 of the cDNA sequence in SEQ ID NO:1 and bases 38–44 are the first 7 bases at the 5'-end of an intron, of about 1700 base pairs in length, between an exon of the GPIa gene, that ends at the base corresponding to base 1458 of the cDNA sequence in SEQ ID NO:1, and an exon of the GPIa that begins at the base corresponding to base 1459 of the cDNA sequence in SEQ ID NO:1.

In SEQ ID NO:9, bases 1–13 are the 13 bases at the 3'-end of the intron, of which the 7 bases at the 5'-end are the final seven bases in SEQ ID NO:8. Bases 14–157 of SEQ ID NO:9 represent an exon of the GPIa gene, which includes the nucleotide, at base 155, that differs in the two Br alleles. Bases 14–157 of SEQ ID NO:9 correspond to bases 1459–1602 in SEQ ID NO:1. Finally, in SEQ ID NO:9, bases 158–390 are the 5'-end of an intron, again about 1700 bases pairs in length, that joins the exon of the GPIa gene ending at the base corresponding to base 1602 in SEQ ID NO:1 and the exon beginning at the base corresponding to base 1603 in SEQ ID NO:1.

In SEQ ID NO:10, bases 1–10 are the 10 bases at the 3'-end of the intron, of which the 233 bases at the 5'-end are the final 233 bases in SEQ ID NO:9. Bases 11–49 of SEQ ID NO:10 correspond to bases 1603–1641 in SEQ ID NO:1.

A preferred primer pair for amplifying a segment of genomic DNA of the GPIa gene is give in SEQ ID NO:11 and SEQ ID NO:12. The primer of SEQ ID NO:11 has the same sequence as bases 1553–1570 in SEQ ID NO:1 and bases 108–125 in SEQ ID NO:9. The primer of SEQ ID NO:12 has the sequence that is the complement of that of bases 372–390 of SEQ ID NO:9.

We note also that bases 115–125 (part of an exon) and bases 286–296 (part of an intron) in SEQ ID NO:9 are restriction sites for MnlI. As indicated above, bases 148–158 in SEQ ID NO:9 is not an MnlI site in the $Br^a$ allele but is in the $Br^b$ allele. Thus, digestion of genomic DNA with MnlI should yield one fragment of 171 base pairs if the allele is $Br^a$ and, in place of this one fragment, two fragments of 33 base pairs and 138 base pairs, respectively, if the allele is $Br^b$ It is to be understood that the above description and examples, while indicating specifics of the invention, are given by way of illustration only, because various changes and modifications within the spirit and scope of the invention will become apparent to those skilled in the art from the discussion and disclosure herein.

We claim:

1. An oligonucleotide which has a sequence selected from the group consisting of (a) a subsequence of 8–50 nucleotides of SEQ ID NO:1, which subsequence includes the A at position 1600 of SEQ ID NO:1; (b) a subsequence of 8–50 nucleotides of the sequence which is the same as SEQ ID NO:1 except that the A at position 1600 is replaced with a G and which subsequence includes the G at position 1600;

(c) a sequence that is fully complementary to that of a subsequence specified in (a); and (d) a sequence that is fully complementary to that of a subsequence specified in (b).

2. An oligononucleotide according to claim 1 which has a sequence of 10–30 nucleotides and is a probe.

3. An oligonucleotide according to claim 1 wherein the oligonucleotide is a DNA.

4. An oligonucleotide according to claim 2 wherein the oligonucleotide is a DNA.

5. A test kit for Br alloantigen typing, comprising:

(a) means for amplifying nucleic acid that comprises at least a portion of a GPIa gene, a GPIa-encoding mRNA, or a GPIa cDNA made from a GPIa-encoding mRNA, wherein the portion comprises a nucleotide that corresponds to the 5'-nucleotide of the codon for the amino acid at position 505 of the mature GPIa subunit corresponding to the gene, mRNA or cDNA of which the portion is a part; and (b) (i) an oligonucleotide probe wherein the sequence of the oligonucleotide is selected from the group consisting of (A) a subsequence of 8–50 nucleotides of SEQ ID NO:1, which subsequence includes the A at position 1600 of SEQ ID NO:1; (B) a subsequence of 8–50 nucleotides of the sequence which is the same as SEQ ID NO:1 except that the A at position 1600 is replaced with a G and which subsequence includes the G at position 1600; (C) a sequence that is fully complementary to that of a subsequence specified in (b)(A); and (d) a sequence that is fully complementary to that of a subsequence specified in (b)(B); or (ii) the restriction endonuclease MnlI.

6. A test kit according to claim 5 wherein the means for amplifying is suitable for amplifying a portion of GPIa-encoding platelet mRNA.

7. A test kit according to claim 6 wherein component (b) is an oligonucleotide probe and wherein the oligonucleotide of the oligonucleotide probe is a DNA of 10–30 nucleotides.

8. A test kit according to claim 6 wherein component (b) is MnlI.

9. A method of Br alloantigen typing comprising the steps of (A) obtaining, by a target nucleic acid amplification process applied to mRNA from human platelets or human genomic DNA, an assayable quantity of amplified nucleic acid with a sequence that is a subsequence, or the full complement of a subsequence, of the mRNA or genomic DNA that encodes a GPIa subunit of a Br alloantigen, said subsequence including the nucleotide at the position in the mRNA or genomic DNA corresponding to the position of 5'-nucleotide of the codon for the amino acid at position 505 of the mature GPIa subunit; and (B) in order to determine the Br alloantigen or Br alloantigens encoded by the mRNA or genomic DNA, analyzing the amplified nucleic acid obtained in step (A) to determine the base or bases at the position in the amplified nucleic acid that corresponds to the position of the 5'-nucleotide of the codon for the amino acid at position 505 of the mature GPIa subunit.

10. The method of claim 9 wherein the amplified nucleic acid is platelet mRNA and the analysis of amplified nucleic acid is by nucleic acid probe hybridization assay with an oligonucleotide probe wherein the sequence of the oligonucleotide is selected from the group consisting of (A) a subsequence of 8–50 nucleotides of SEQ ID NO:1, which subsequence includes the A at position 1600 of SEQ ID NO:1; (B) a subsequence of 8–50 nucleotides of the sequence which is the same as SEQ ID NO:1 except that the A at position 1600 is replaced with a G and which subsequence includes the G at position 1600; (C) a sequence that is fully complementary to that of a subsequence specified in (A); and (d) a sequence that is fully complementary to that of a subsequence specified in (B).

11. The method of claim 10 wherein the oligonucleotide of the probe is a DNA and has 10–30 bases.

12. The method of claim 10 wherein the amplification of the platelet mRNA is by the PCR method.

13. The method of claim 12 wherein the oligonucleotide of the probe is a DNA and has 10–30 bases.

14. The method of claim 9 wherein the amplified nucleic acid is platelet mRNA, wherein the amplification of the platelet mRNA is by the PCR method, and wherein the analysis of the DNA resulting from the PCR amplification comprises (i) incubation of said DNA with MnlI under conditions whereby the DNA will be cleaved by the MnlI if the DNA comprises a recognition site for the enzyme followed by (ii) size analysis of the DNA to determine whether the DNA includes a recognition site for the enzyme characteristic of cDNA made from mRNA encoding the GPIa subunit of the $Br^b$ alloantigen.

15. In combination in an aqueous solution, a pair of oligonucleotide primers for the amplification by the PCR process of a segment of platelet mRNA which encodes a GPIa or a segment of genomic DNA for GPIa, said oligonucleotide primers being selected from the group consisting of DNAs with the sequences of SEQ ID NO:2–SEQ ID NO:5, SEQ ID NO:11 and SEQ ID NO:12.

16. A method of amplifying platelet mRNA which comprises amplification by the PCR method employing as primers a pair of oligonucleotide primers for the amplification by the PCR process of a segment of platelet mRNA which encodes a GPIa subunit, said oligonucleotide primers being selected from the group consisting of DNAs with the sequences of SEQ ID NO:2–SEQ ID NO:5.

* * * * *

UNITED STATES PATENT AND TRADEMARK OFFICE
CERTIFICATE OF CORRECTION

PATENT NO. : 5,516,634  
DATED : May 14, 1996  
INVENTOR(S) : Newman et al.

Page 1 of 4

It is certified that error appears in the above-indentified patent and that said Letters Patent is hereby corrected as shown below: Title page, item [54], and column 1, Title should read --MOLECULAR BASIS OF THE HUMAN PLATELET $Br^a/Br^b$ ALLOANTIGEN SYSTEM AND APPLICATIONS THEREOF.

In column 4, line 9 of the patent, "Bra-" should be --$Br^a$- --.

In column 4, line 10 of the patent, "$Br_b$-encoding" should be --$Br^b$-encoding--.

In column 6, line 28 of the patent, "SEQ ID NO:I" should be --SEQ ID NO:1--.

In column 12, lines 2-4 of the patent, "GPIa Subunit" should occur immediately after "Determinants to the".

In column 12, line 24 of the patent, "Brb" should be --$Br^b$--.

In column 12, lines 41-42 of the patent, "precipitating GPIIa." should be deleted.

Table 1 in Column 13 of the patent, should have --±-- in place of each occurrence of "+".

In column 14, line 15 of the patent, "50 $\mu$l" should be --50 $\mu$l.--.

In column 15, lines 15-16 of the patent, the word "München," should be kept together on the same line.

UNITED STATES PATENT AND TRADEMARK OFFICE
CERTIFICATE OF CORRECTION

PATENT NO. : 5,516,634  Page 2 of 4
DATED : May 14, 1996
INVENTOR(S) : Newman et al.

It is certified that error appears in the above-indentified patent and that said Letters Patent is hereby corrected as shown below:

In column 15, line 19 of the patent, "15%" should be --5%--.

Table 2 in column 15 of the patent, should have --±-- in place of each occurrence of "+".

In column 16, lines 58-59 of the patent, the period after "$Br^b$" should appear on the same line as "$Br^b$".

In the sequence listing appearing in columns 17 and 18 of the patent, section (2) (X) (B) "Title", "Receptor Prine '2 Subunit" should read --Receptor $\alpha^2$ Subunit--.

In column 21 (Sequence Listing) of the patent, "(2) INFORMATION FOR SEQ ID NO:2:" should be --(3) INFORMATION FOR SEQ ID NO:2:--.

In column 21 (Sequence Listing) of the patent, "(2) INFORMATION FOR SEQ ID NO:3:" should be --(4) INFORMATION FOR SEQ ID NO:3:--.

In column 23 (Sequence Listing) of the patent, "(2) INFORMATION FOR SEQ ID NO:4:" should be --(5) INFORMATION FOR SEQ ID NO:4:--.

In column 23 (Sequence Listing) of the patent, "(2) INFORMATION FOR SEQ ID NO:5:" should be --(6) INFORMATION FOR SEQ ID NO:5:--.

UNITED STATES PATENT AND TRADEMARK OFFICE
CERTIFICATE OF CORRECTION

Page 3 of 4

PATENT NO. : 5,516,634
DATED : May 14, 1996
INVENTOR(S) : Newman et al.

It is certified that error appears in the above-indentified patent and that said Letters Patent is hereby corrected as shown below:

In column 23 (Sequence Listing) of the patent, "(2) INFORMATION FOR SEQ ID NO:6:" should be --(7) INFORMATION FOR SEQ ID NO:6:--.

In column 23 (Sequence Listing) of the patent, "(2) INFORMATION FOR SEQ ID NO:7:" should be --(8) INFORMATION FOR SEQ ID NO:7:--.

In column 23 (Sequence Listing) of the patent, "(2) INFORMATION FOR SEQ ID NO:8:" should be --(9) INFORMATION FOR SEQ ID NO:8:--.

In column 23 (Sequence Listing) of the patent, "(2) INFORMATION FOR SEQ ID NO:9:" should be --(10) INFORMATION FOR SEQ ID NO:9:--.

In column 25 (Sequence Listing) of the patent, "(2) INFORMATION FOR SEQ ID NO:10:" should be --(11) INFORMATION FOR SEQ ID NO:10:--.

In column 25 (Sequence Listing) of the patent, "(2) INFORMATION FOR SEQ ID NO:11:" should be --(12) INFORMATION FOR SEQ ID NO:11:--.

UNITED STATES PATENT AND TRADEMARK OFFICE
CERTIFICATE OF CORRECTION

PATENT NO. : 5,516,634
DATED : May 14, 1996
INVENTOR(S) : Newman, et. al.

It is certified that error appears in the above-indentified patent and that said Letters Patent is hereby corrected as shown below:

In column 25 (Sequence Listing) of the patent, "(2) INFORMATION FOR SEQ ID NO:12" should be -- (13) INFORMATION FOR SEQ ID NO:12:--.

Signed and Sealed this

Eighth Day of April, 1997

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 3546 base pairs
    ( B ) TYPE: nucleic acid
    ( C ) STRANDEDNESS: double
    ( D ) TOPOLOGY: linear ( i i ) MOLECULE TYPE: cDNA to mRNA ( x ) PUBLICATION INFORMATION:
    ( A ) AUTHORS: TAKADA, Y.
           HEMLER, M. E.
    ( B ) TITLE: The Primary Structure of the
           VLA- 2/Collagen Receptor '2 Subunit
           ( P l a t e l e t   G P I a ): Homology to Other
           Integrins and the Presence of a
           Possible Collagen-binding Domain
    ( C ) JOURNAL: J. Cell Biol.
    ( D ) VOLUME: 109
    ( F ) PAGES: 397-407
    ( G ) DATE: July-1989
    ( K ) RELEVANT RESIDUES IN SEQ ID NO:1: FROM 1 TO 3546

( x i ) SEQUENCE DESCRIPTION: SEQ ID NO:1:

| | | | | |
|---|---|---|---|---|
| ATGGGGCCAG | AACGGACAGG | GGCCGCGCCG | | 30 |
| CTGCCGCTGC | TGCTGGTGTT | AGCGCTCAGT | CAAGGCATTT | 70 |
| TAAATTGTTG | TTTGGCCTAC | AATGTTGGTC | TCCCAGAAGC | 110 |
| AAAAATATTT | TCCGGTCCTT | CAAGTGAACA | GTTTGGGTAT | 150 |
| GCAGTGCAGC | AGTTTATAAA | TCCAAAAGGC | AACTGGTTAC | 190 |
| TGGTTGGTTC | ACCCTGGAGT | GGCTTTCCTG | AGAACCGAAT | 230 |
| GGGAGATGTG | TATAAATGTC | CTGTTGACCT | ATCCACTGCC | 270 |
| ACATGTGAAA | AACTAAATTT | GCAAACTTCA | ACAAGCATTC | 310 |
| CAAATGTTAC | TGAGATGAAA | ACCAACATGA | GCCTCGGCTT | 350 |
| GATCCTCACC | AGGAACATGG | GAACTGGAGG | TTTTCTCACA | 390 |
| TGTGGTCCTC | TGTGGGCACA | GCAATGTGGG | AATCAGTATT | 430 |
| ACACAACGGG | TGTGTGTTCT | GACATCAGTC | CTGATTTTCA | 470 |
| GCTCTCAGCC | AGCTTCTCAC | CTGCAACTCA | GCCCTGCCCT | 510 |
| TCCCTCATAG | ATGTTGTGGT | TGTGTGTGAT | GAATCAAATA | 550 |
| GTATTTATCC | TTGGGATGCA | GTAAAGAATT | TTTTGGAAAA | 590 |
| ATTTGTACAA | GGCCTTGATA | TAGGCCCCAC | AAAGACACAG | 630 |
| GTGGGGTTAA | TTCAGTATGC | CAATAATCCA | AGAGTTGTGT | 670 |
| TTAACTTGAA | CACATATAAA | ACCAAAGAAG | AAATGATTGT | 710 |
| AGCAACATCC | CAGACATCCC | AATATGGTGG | GGACCTCACA | 750 |
| AACACATTCG | GAGCAATTCA | ATATGCAAGA | AAATATGCCT | 790 |
| ATTCAGCAGC | TTCTGGTGGG | CGACGAAGTG | CTACGAAAGT | 830 |
| AATGGTAGTT | GTAACTGACG | GTGAATCACA | TGATGGTTCA | 870 |
| ATGTTGAAAG | CTGTGATTGA | TCAATGCAAC | CATGACAATA | 910 |

| | | | | |
|---|---|---|---|---|
| TACTGAGGTT | TGGCATAGCA | GTTCTTGGGT | ACTTAAACAG | 950 |
| AAACGCCCTT | GATACTAAAA | ATTTAATAAA | AGAAATAAAA | 990 |
| GCGATCGCTA | GTATTCCAAC | AGAAAGATAC | TTTTTCAATG | 1030 |
| TGTCTGATGA | AGCAGCTCTA | CTAGAAAAGG | CTGGGACATT | 1070 |
| AGGAGAACAA | ATTTTCAGCA | TTGAAGGTAC | TGTTCAAGGA | 1110 |
| GGAGACAACT | TTCAGATGGA | AATGTCACAA | GTGGGATTCA | 1150 |
| GTGCAGATTA | CTCTTCTCAA | AATGATATTC | TGATGCTGGG | 1190 |
| TGCAGTGGGA | GCTTTTGGCT | GGAGTGGGAC | CATTGTCCAG | 1230 |
| AAGACATCTC | ATGGCCATTT | GATCTTTCCT | AAACAAGCCT | 1270 |
| TTGACCAAAT | TCTGCAGGAC | AGAAATCACA | GTTCATATTT | 1310 |
| AGGTTACTCT | GTGGCTGCAA | TTTCTACTGG | AGAAAGCACT | 1350 |
| CACTTTGTTG | CTGGTGCTCC | TCGGGCAAAT | TATACCGGCC | 1390 |
| AGATAGTGCT | ATATAGTGTG | AATGAGAATG | GCAATATCAC | 1430 |
| GGTTATTCAG | GCTCACCGAG | GTGACCAGAT | TGGCTCCTAT | 1470 |
| TTTGGTAGTG | TGCTGTGTTC | AGTTGATGTG | GATAAAGACA | 1510 |
| CCATTACAGA | CGTGCTCTTG | GTAGGTGCAC | CAATGTACAT | 1550 |
| GAGTGACCTA | AAGAAAGAGG | AAGGAAGAGT | CTACCTGTTT | 1590 |
| ACTATCAAAA | AGGGCATTTT | GGGTCAGCAC | CAATTTCTTG | 1630 |
| AAGGCCCCGA | GGGCATTGAA | AACACTCGAT | TTGGTTCAGC | 1670 |
| AATTGCAGCT | CTTTCAGACA | TCAACATGGA | TGGCTTTAAT | 1710 |
| GATGTGATTG | TTGGTTCACC | ACTAGAAAAT | CAGAATTCTG | 1750 |
| GAGCTGTATA | CATTTACAAT | GGTCATCAGG | GCACTATCCG | 1790 |
| CACAAAGTAT | TCCCAGAAAA | TCTTGGGATC | CGATGGAGCC | 1830 |
| TTTAGGAGCC | ATCTCCAGTA | CTTTGGGAGG | TCCTTGGATG | 1870 |
| GCTATGGAGA | TTTAAATGGG | GATTCCATCA | CCGATGTGTC | 1910 |
| TATTGGTGCC | TTTGGACAAG | TGGTTCAACT | CTGGTCACAA | 1950 |
| AGTATTGCTG | ATGTAGCTAT | AGAAGCTTCA | TTCACACCAG | 1990 |
| AAAAAATCAC | TTTGGTCAAC | AAGAATGCTC | AGATAATTCT | 2030 |
| CAAACTCTGC | TTCAGTGCAA | AGTTCAGACC | TACTAAGCAA | 2070 |
| AACAATCAAG | TGGCCATTGT | ATATAACATC | ACACTTGATG | 2110 |
| CAGATGGATT | TTCATCCAGA | GTAACCTCCA | GGGGGTTATT | 2150 |
| TAAAGAAAAC | AATGAAAGGT | GCCTGCAGAA | GAATATGGTA | 2190 |
| GTAAATCAAG | CACAGAGTTG | CCCCGAGCAC | ATCATTTATA | 2230 |
| TACAGGAGCC | CTCTGATGTT | GTCAACTCTT | TGGATTTGCG | 2270 |
| TGTGGACATC | AGTCTGGAAA | ACCCTGGCAC | TAGCCCTGCC | 2310 |
| CTTGAAGCCT | ATTCTGAGAC | TGCCAAGGTC | TTCAGTATTC | 2350 |
| CTTTCCACAA | AGACTGTGGT | GAGGATGGAC | TTTGCATTTC | 2390 |
| TGATCTAGTC | CTAGATGTCC | GACAAATACC | AGCTGCTCAA | 2430 |
| GAACAACCCT | TTATTGTCAG | CAACCAAAAC | AAAAGGTTAA | 2470 |
| CATTTTCAGT | AACACTGAAA | AATAAAAGGG | AAAGTGCATA | 2510 |

-continued

| | | | | |
|---|---|---|---|---|
| CAACACTGGA | ATTGTTGTTG | ATTTTTCAGA | AAACTTGTTT | 2550 |
| TTTGCATCAT | TCTCCCTACC | GGTTGATGGG | ACAGAAGTAA | 2590 |
| CATGCCAGGT | GGCTGCATCT | CAGAAGTCTG | TTGCCTGCGA | 2630 |
| TGTAGGCTAC | CCTGCTTTAA | AGAGAGAACA | ACAGGTGACT | 2670 |
| TTTACTATTA | ACTTTGACTT | CAATCTTCAA | AACCTTCAGA | 2710 |
| ATCAGGCGTC | TCTCAGTTTC | CAAGCCTTAA | GTGAAAGCCA | 2750 |
| AGAAGAAAAC | AAGGCTGATA | ATTTGGTCAA | CCTCAAAATT | 2790 |
| CCTCTCCTGT | ATGATGCTGA | AATTCACTTA | ACAAGATCTA | 2830 |
| CCAACATAAA | TTTTTATGAA | ATCTCTTCGG | ATGGGAATGT | 2870 |
| TCCTTCAATC | GTGCACAGTT | TTGAAGATGT | TGGTCCAAAA | 2910 |
| TTCATCTTCT | CCCTGAAGGT | AACAACAGGA | AGTGTTCCAG | 2950 |
| TAAGCATGGC | AACTGTAATC | ATCCACATCC | CTCAGTATAC | 2990 |
| CAAAGAAAAG | AACCCACTGA | TGTACCTAAC | TGGGGTGCAA | 3030 |
| ACAGACAAGG | CTGGTGACAT | CAGTTGTAAT | GCAGATATCA | 3070 |
| ATCCACTGAA | AATAGGACAA | ACATCTTCTT | CTGTATCTTT | 3110 |
| CAAAAGTGAA | AATTTCAGGC | ACACCAAAGA | ATTGAACTGC | 3150 |
| AGAACTGCTT | CCTGTAGTAA | TGTTACCTGC | TGGTTGAAAG | 3190 |
| ACGTTCACAT | GAAAGGAGAA | TACTTTGTTA | ATGTGACTAC | 3230 |
| CAGAATTTGG | AACGGGACTT | TCGCATCATC | AACGTTCCAG | 3270 |
| ACAGTACAGC | TAACGGCAGC | TGCAGAAATC | AACACCTATA | 3310 |
| ACCCTGAGAT | ATATGTGATT | GAAGATAACA | CTGTTACGAT | 3350 |
| TCCCCTGATG | ATAATGAAAC | CTGATGAGAA | AGCCGAAGTA | 3390 |
| CCAACAGGAG | TTATAATAGG | AAGTATAATT | GCTGGAATCC | 3430 |
| TTTTGCTGTT | AGCTCTGGTT | GCAATTTTAT | GGAAGCTCGG | 3470 |
| CTTCTTCAAA | AGAAAATATG | AAAAGATGAC | CAAAAATCCA | 3510 |
| GATGAGATTG | ATGAGACCAC | AGAGCTCAGT | AGCTGA | 3546 |

(2) INFORMATION FOR SEQ ID NO:2:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:2:

CAATATCACG GTTATTCAGG CTCACC    26

(2) INFORMATION FOR SEQ ID NO:3:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:3:

CCCATTTAAA TCTCCATAGC CATCC                                                                25

( 2 ) INFORMATION FOR SEQ ID NO:4:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:4:

CAGGCTCACC GAGGTGACCA GATTGGC                                                              27

( 2 ) INFORMATION FOR SEQ ID NO:5:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:5:

AGTACTGGAG ATGGCTCCTA                                                                      20

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:6:

TATCAAAGAG G                                                                               11

( 2 ) INFORMATION FOR SEQ ID NO:7:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:7:

TATCAAAAAG G                                                                               11

( 2 ) INFORMATION FOR SEQ ID NO:8:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:8:

CAATATCACG GTTATTCAGG CTCACCGAGG TGACCAGGTA AATC                                            44

( 2 ) INFORMATION FOR SEQ ID NO:9:

(i) SEQUENCE CHARACTERISTICS:
    (A) LENGTH: 390 base pairs
    (B) TYPE: nucleic acid
    (C) STRANDEDNESS: double
    (D) TOPOLOGY: linear (ii) MOLECULE TYPE: Genomic DNA (xi) SEQUENCE DESCRIPTION: SEQ ID NO:9:

```
TTTATTACTC  CAGATTGGCT  CCTATTTTGG  TAGTGTGCTG                    40
TGTTCAGTTG  ATGTGGATAA  AGACACCATT  ACAGACGTGC                    80
TCTTGGTAGG  TGCACCAATG  TACATGAGTG  ACCTAAAGAA                   120
AGAGGAAGGA  AGAGTCTACC  TGTTTACTAT  CAAAAAGGTA                   160
AAAAAAAAAA  AATAAACTAA  ATAGTTTAAT  TTGCTTTTAG                   200
TACTGGTAAT  TTAACTTGCA  TTTGGAAAGA  AAAATTTATT                   240
ATTATTGAAT  GATAATTTGC  ACAGATAGTA  TGGTTTACAT                   280
TTCATCATTT  TTGAGGTATG  CCCATTAAGT  TATGATTTTA                   320
AAAATCACAT  TAACAGGAAA  AAAAAAAAAC  TAGAGTTGAA                   360
TGTATAGTGT  ACTGCCATTT  TCCATGAGAG                                390
```

(2) INFORMATION FOR SEQ ID NO:10:

(i) SEQUENCE CHARACTERISTICS:
       (A) LENGTH: 49 base pairs
       (B) TYPE: nucleic acid
       (C) STRANDEDNESS: double
       (D) TOPOLOGY: linear (ii) MOLECULE TYPE: Genomic DNA (xi) SEQUENCE DESCRIPTION: SEQ ID NO:10:

```
CCTTTGCAAG  GGCATTTTGG  GTCAGCACCA  ATTTCTTGAA  GGCCCCGAG         49
```

(2) INFORMATION FOR SEQ ID NO:11:

(i) SEQUENCE CHARACTERISTICS:
       (A) LENGTH: 18 bases
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:11:

```
GTGACCTAAA  GAAAGAGG                                              18
```

(2) INFORMATION FOR SEQ ID NO:12:

(i) SEQUENCE CHARACTERISTICS:
       (A) LENGTH: 19 bases
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:12:

```
CTCTCATGGA  AAATGGCAG                                             19
```